（12） United States Patent
Hoey et al.

(10) Patent No.: US 8,801,702 B2
(45) Date of Patent: Aug. 12, 2014

(54) SYSTEMS AND METHODS FOR TREATMENT OF BPH

(71) Applicant: NxThera, Inc., Maple Grove, MN (US)

(72) Inventors: Michael Hoey, Shoreview, MN (US); John H. Shadduck, Menlo Park, CA (US)

(73) Assignee: NxThera, Inc., Maple Grove, MN (US)

( * ) Notice: Subject to any disclaimer, the term of this patent is extended or adjusted under 35 U.S.C. 154(b) by 0 days.

(21) Appl. No.: 13/764,645

(22) Filed: Feb. 11, 2013

(65) Prior Publication Data
US 2013/0158534 A1 Jun. 20, 2013

Related U.S. Application Data

(62) Division of application No. 12/614,226, filed on Nov. 6, 2009, now Pat. No. 8,372,065.

(60) Provisional application No. 61/112,103, filed on Nov. 6, 2008.

(51) Int. Cl.
A61B 18/04 (2006.01)
A61B 17/3203 (2006.01)
A61B 17/3205 (2006.01)
A61B 18/14 (2006.01)
A61B 17/22 (2006.01)
A61B 18/00 (2006.01)
A61B 17/00 (2006.01)

(52) U.S. Cl.
CPC ............ A61B 18/04 (2013.01); A61B 17/32037 (2013.01); A61B 2017/22079 (2013.01); A61B 2018/00577 (2013.01); A61B 2018/00547 (2013.01); A61B 2018/048 (2013.01); A61B 2017/00274 (2013.01); A61B 17/32056 (2013.01); A61B 18/1485 (2013.01); A61B 2017/22067 (2013.01)
USPC ................................. 606/27; 606/41; 604/514

(58) Field of Classification Search
USPC ....................... 606/27, 41; 607/104, 105, 113; 604/113, 22, 500, 517
See application file for complete search history.

(56) References Cited

U.S. PATENT DOCUMENTS 4,672,963 A 6/1987 Barken
4,920,982 A 5/1990 Goldstein
(Continued)

FOREIGN PATENT DOCUMENTS

CN 2061443 U 9/1990
CN 101072544 11/2007
(Continued)

OTHER PUBLICATIONS

Hai; Photoselective Vaporization Prostatectomy: A Palliative Treatment Option for Men with Urinary Obstruction Secondary to Prostate Cancer; PCRI Prost.Cancer Rsrch.Inst. Reprint.from PCRI Insights Nov. 2005, vol. 8(4); Dwnld from http://www.prostate-cancer.org/pcricms/node/233 on May 10, 2012; 4 pages.

(Continued)

Primary Examiner — Linda Dvorak
Assistant Examiner — Jocelyn D Ram
(74) Attorney, Agent, or Firm — Shay Glenn LLP

(57) ABSTRACT

A prostate therapy system is provided that may include any of a number of features. One feature of the prostate therapy system is that it can access a prostate lobe from the urethra. Another feature of the prostate therapy system is that it can deliver condensable vapor into the prostate to ablate the prostate tissue. Another feature of the prostate therapy system is that it can aspirate tissue from the prostate. Yet another feature of the prostate therapy system is that it can rotate during delivery of vapor and aspiration of tissue. Methods associated with use of the prostate therapy system are also covered.

7 Claims, 6 Drawing Sheets

(56) References Cited

U.S. PATENT DOCUMENTS

| | | | |
|---|---|---|---|
| 4,950,267 A | 8/1990 | Ishihara et al. | |
| 5,117,482 A | 5/1992 | Hauber | |
| 5,222,185 A | 6/1993 | McCord, Jr. | |
| 5,312,399 A * | 5/1994 | Hakky et al. | 606/15 |
| 5,330,518 A | 7/1994 | Neilson et al. | |
| 5,366,490 A | 11/1994 | Edwards et al. | |
| 5,370,609 A | 12/1994 | Drasler et al. | |
| 5,370,675 A * | 12/1994 | Edwards et al. | 607/101 |
| 5,385,544 A | 1/1995 | Edwards et al. | |
| 5,409,453 A | 4/1995 | Lundquist et al. | |
| 5,421,819 A | 6/1995 | Edwards et al. | |
| 5,435,805 A | 7/1995 | Edwards et al. | |
| 5,470,308 A | 11/1995 | Edwards et al. | |
| 5,470,309 A | 11/1995 | Edwards et al. | |
| 5,484,400 A | 1/1996 | Edwards et al. | |
| 5,499,998 A | 3/1996 | Meade | |
| 5,531,676 A | 7/1996 | Edwards et al. | |
| 5,542,915 A | 8/1996 | Edwards et al. | |
| 5,542,916 A | 8/1996 | Hirsch et al. | |
| 5,545,171 A | 8/1996 | Sharkey et al. | |
| 5,549,644 A | 8/1996 | Lundquist et al. | |
| 5,554,110 A | 9/1996 | Edwards et al. | |
| 5,556,377 A | 9/1996 | Rosen et al. | |
| 5,558,673 A | 9/1996 | Edwards et al. | |
| 5,588,960 A | 12/1996 | Edwards et al. | |
| 5,591,125 A | 1/1997 | Edwards et al. | |
| 5,599,294 A | 2/1997 | Edwards et al. | |
| 5,601,591 A | 2/1997 | Edwards et al. | |
| 5,630,794 A | 5/1997 | Lax et al. | |
| 5,667,488 A | 9/1997 | Lundquist et al. | |
| 5,672,153 A | 9/1997 | Lax et al. | |
| 5,709,680 A | 1/1998 | Yates et al. | |
| 5,720,718 A | 2/1998 | Rosen et al. | |
| 5,720,719 A | 2/1998 | Edwards et al. | |
| 5,797,903 A | 8/1998 | Swanson et al. | |
| 5,800,486 A * | 9/1998 | Thome et al. | 607/105 |
| 5,830,179 A | 11/1998 | Mikus et al. | |
| 5,849,011 A | 12/1998 | Jones et al. | |
| 5,871,481 A | 2/1999 | Kannenberg et al. | |
| 5,873,877 A | 2/1999 | McGaffigan et al. | |
| 5,897,553 A | 4/1999 | Mulier et al. | |
| 5,944,715 A | 8/1999 | Goble et al. | |
| 5,957,922 A | 9/1999 | Imran | |
| 5,964,752 A * | 10/1999 | Stone | 606/27 |
| 5,964,756 A | 10/1999 | McGaffigan et al. | |
| 5,976,123 A | 11/1999 | Baumgardner et al. | |
| 5,990,465 A | 11/1999 | Nakaoka et al. | |
| 6,007,571 A * | 12/1999 | Neilson et al. | 607/105 |
| 6,017,358 A | 1/2000 | Yoon et al. | |
| 6,017,361 A | 1/2000 | Mikus et al. | |
| 6,036,713 A | 3/2000 | Kieturakis | |
| 6,063,081 A | 5/2000 | Mulier et al. | |
| 6,077,257 A * | 6/2000 | Edwards et al. | 604/506 |
| 6,113,593 A | 9/2000 | Tu et al. | |
| 6,147,336 A | 11/2000 | Ushijima et al. | |
| 6,179,836 B1 * | 1/2001 | Eggers et al. | 606/45 |
| 6,206,847 B1 | 3/2001 | Edwards et al. | |
| 6,231,591 B1 | 5/2001 | Desai | |
| 6,238,389 B1 | 5/2001 | Paddock et al. | |
| 6,238,391 B1 | 5/2001 | Olsen et al. | |
| 6,241,702 B1 | 6/2001 | Lundquist et al. | |
| 6,258,087 B1 | 7/2001 | Edwards et al. | |
| 6,287,297 B1 | 9/2001 | Woodruff et al. | |
| 6,423,027 B1 * | 7/2002 | Gonon | 604/27 |
| 6,440,127 B2 | 8/2002 | McGovern et al. | |
| 6,517,534 B1 | 2/2003 | McGovern et al. | |
| 6,524,270 B1 * | 2/2003 | Bolmsjo et al. | 604/22 |
| 6,544,211 B1 * | 4/2003 | Andrew et al. | 604/28 |
| 6,551,300 B1 | 4/2003 | McGaffigan | |
| 6,565,561 B1 * | 5/2003 | Goble et al. | 606/41 |
| 6,575,968 B1 * | 6/2003 | Eggers et al. | 606/41 |
| 6,607,529 B1 | 8/2003 | Jones et al. | |
| 6,638,275 B1 | 10/2003 | McGaffigan et al. | |
| 6,669,694 B2 | 12/2003 | Shadduck | |
| 6,716,252 B2 | 4/2004 | Lazarovitz et al. | |
| 6,719,738 B2 | 4/2004 | Mehier | |
| 6,726,696 B1 | 4/2004 | Houser et al. | |
| 6,730,079 B2 | 5/2004 | Lovewell | |
| 6,760,616 B2 | 7/2004 | Hoey et al. | |
| 6,780,178 B2 | 8/2004 | Palanker et al. | |
| 6,827,718 B2 | 12/2004 | Hutchins et al. | |
| 6,905,475 B2 | 6/2005 | Hauschild et al. | |
| 6,969,376 B2 | 11/2005 | Takagi et al. | |
| 6,974,455 B2 | 12/2005 | Garabedian et al. | |
| 7,014,652 B2 | 3/2006 | Cioanta et al. | |
| 7,041,121 B1 | 5/2006 | Williams et al. | |
| 7,066,935 B2 | 6/2006 | Swoyer et al. | |
| 7,089,064 B2 | 8/2006 | Manker et al. | |
| 7,130,697 B2 | 10/2006 | Chornenky et al. | |
| 7,261,709 B2 | 8/2007 | Swoyer et al. | |
| 7,261,710 B2 | 8/2007 | Elmouelhi et al. | |
| 7,335,197 B2 | 2/2008 | Sage et al. | |
| 7,429,262 B2 | 9/2008 | Woloszko et al. | |
| 7,470,228 B2 | 12/2008 | Connors et al. | |
| 7,674,259 B2 * | 3/2010 | Shadduck | 606/41 |
| 7,959,577 B2 | 6/2011 | Schmitz et al. | |
| 8,016,823 B2 * | 9/2011 | Shadduck | 606/41 |
| 8,216,217 B2 * | 7/2012 | Sharkey et al. | 606/27 |
| 8,221,403 B2 * | 7/2012 | Sharkey et al. | 606/27 |
| 8,244,327 B2 | 8/2012 | Fichtinger et al. | |
| 8,251,985 B2 * | 8/2012 | Hoey et al. | 606/27 |
| 8,272,383 B2 | 9/2012 | Hoey et al. | |
| 8,273,079 B2 * | 9/2012 | Hoey et al. | 606/27 |
| 8,313,485 B2 * | 11/2012 | Shadduck | 606/41 |
| 8,372,065 B2 | 2/2013 | Hoey et al. | |
| 8,388,611 B2 | 3/2013 | Shadduck et al. | |
| 8,409,109 B2 | 4/2013 | Tiesma et al. | |
| 8,419,723 B2 | 4/2013 | Shadduck et al. | |
| 8,550,743 B2 | 10/2013 | Bonde et al. | |
| 2002/0078956 A1 | 6/2002 | Sharpe et al. | |
| 2002/0177846 A1 * | 11/2002 | Mulier et al. | 606/27 |
| 2003/0069575 A1 | 4/2003 | Chin et al. | |
| 2003/0097126 A1 | 5/2003 | Woloszko et al. | |
| 2003/0130575 A1 | 7/2003 | Desai | |
| 2003/0206730 A1 | 11/2003 | Golan | |
| 2004/0068306 A1 | 4/2004 | Shadduck | |
| 2004/0230316 A1 | 11/2004 | Cioanta et al. | |
| 2005/0096629 A1 | 5/2005 | Gerber et al. | |
| 2005/0124915 A1 | 6/2005 | Eggers et al. | |
| 2005/0149020 A1 | 7/2005 | Jahng | |
| 2005/0159676 A1 | 7/2005 | Taylor et al. | |
| 2006/0135955 A1 * | 6/2006 | Shadduck | 606/27 |
| 2006/0178670 A1 | 8/2006 | Woloszko et al. | 606/48 |
| 2006/0224154 A1 * | 10/2006 | Shadduck et al. | 606/41 |
| 2006/0224169 A1 | 10/2006 | Weisenburgh, II et al. | |
| 2006/0253069 A1 | 11/2006 | Li et al. | |
| 2006/0276871 A1 | 12/2006 | Lamson et al. | |
| 2007/0032785 A1 | 2/2007 | Diederich et al. | |
| 2007/0142846 A1 | 6/2007 | Catanese, III et al. | |
| 2007/0179491 A1 | 8/2007 | Kratoska et al. | |
| 2008/0021484 A1 | 1/2008 | Catanese, III et al. | |
| 2008/0021485 A1 | 1/2008 | Catanese, III et al. | |
| 2008/0033232 A1 | 2/2008 | Catanese, III et al. | |
| 2008/0033458 A1 | 2/2008 | McLean et al. | |
| 2008/0033488 A1 | 2/2008 | Catanese, III et al. | |
| 2008/0039833 A1 | 2/2008 | Catanese, III et al. | |
| 2008/0039872 A1 | 2/2008 | Catanese, III et al. | |
| 2008/0039874 A1 | 2/2008 | Catanese, III et al. | |
| 2008/0039875 A1 | 2/2008 | Catanese, III et al. | |
| 2008/0039876 A1 | 2/2008 | Catanese, III et al. | |
| 2008/0039893 A1 | 2/2008 | McLean et al. | |
| 2008/0039894 A1 | 2/2008 | Catanese, III et al. | |
| 2008/0046045 A1 | 2/2008 | Yon et al. | |
| 2008/0132826 A1 | 6/2008 | Shadduck et al. | |
| 2008/0188811 A1 | 8/2008 | Kim | |
| 2008/0208187 A1 | 8/2008 | Bhushan et al. | |
| 2008/0249399 A1 | 10/2008 | Appling et al. | |
| 2008/0262491 A1 | 10/2008 | Swoyer et al. | |
| 2008/0269737 A1 | 10/2008 | Elmouelhi et al. | |
| 2008/0269862 A1 | 10/2008 | Elmouelhi et al. | |
| 2008/0275440 A1 | 11/2008 | Kratoska et al. | |
| 2008/0297287 A1 | 12/2008 | Shachar et al. | |
| 2008/0312497 A1 | 12/2008 | Elmouelhi et al. | |
| 2009/0018553 A1 | 1/2009 | McLean et al. | |

(56) References Cited

U.S. PATENT DOCUMENTS

| | | |
|---|---|---|
| 2009/0054871 A1 | 2/2009 | Sharkey et al. |
| 2009/0138001 A1 | 5/2009 | Barry et al. |
| 2009/0149846 A1 | 6/2009 | Hoey et al. |
| 2009/0216220 A1 | 8/2009 | Hoey et al. |
| 2009/0227998 A1 | 9/2009 | Aljuri et al. |
| 2009/0306640 A1 | 12/2009 | Glaze et al. |
| 2010/0016757 A1 | 1/2010 | Greenburg et al. |
| 2010/0049031 A1 | 2/2010 | Fruland et al. |
| 2010/0094270 A1 | 4/2010 | Sharma |
| 2010/0114083 A1 | 5/2010 | Sharma |
| 2010/0179416 A1 | 7/2010 | Hoey et al. |
| 2010/0193568 A1 | 8/2010 | Scheib et al. |
| 2010/0204688 A1 | 8/2010 | Hoey et al. |
| 2010/0262137 A1 | 10/2010 | Nye et al. |
| 2010/0286679 A1 | 11/2010 | Hoey et al. |
| 2010/0292767 A1 | 11/2010 | Hoey et al. |
| 2010/0298948 A1 | 11/2010 | Hoey et al. |
| 2011/0060328 A1 | 3/2011 | Skwarek et al. |
| 2011/0238144 A1 | 9/2011 | Hoey et al. |
| 2011/0319759 A1 | 12/2011 | Liu et al. |
| 2012/0259271 A1 * | 10/2012 | Shadduck et al. .............. 604/24 |
| 2012/0265276 A1 * | 10/2012 | Curley ............................ 607/98 |
| 2012/0283717 A1 * | 11/2012 | Sharkey et al. ................. 606/27 |
| 2012/0323167 A1 | 12/2012 | Hoey et al. |
| 2013/0006231 A1 * | 1/2013 | Sharma et al. .................. 606/27 |
| 2013/0074847 A1 | 3/2013 | Hoey et al. |

FOREIGN PATENT DOCUMENTS

| | | |
|---|---|---|
| JP | 2001-500763 A | 1/2001 |
| WO | WO 92/10142 A1 | 6/1992 |
| WO | WO 01/24715 A1 | 4/2001 |
| WO | WO 03/088851 A1 | 10/2003 |
| WO | WO 2006/004482 A1 | 1/2006 |
| WO | WO 2008/083407 A1 | 7/2008 |

OTHER PUBLICATIONS

Shadduck et al.; U.S. Appl. No. 13/779,616 entitled "Systems and Methods for Treatment of Prostatic Tissue," filed Feb. 27, 2013.

Shadduck et al.; U.S. Appl. No. 13/861,109 entitled "Systems and Methods for Treatment of Prostatic Tissue," filed Apr. 11, 2013.

* cited by examiner

SYSTEMS AND METHODS FOR TREATMENT OF BPH

CROSS REFERENCE TO RELATED APPLICATIONS

This application is a divisional of U.S. application Ser. No. 12/614,226, filed Nov. 6, 2009, now U.S. Pat. No. 8,372,065; which application claims the benefit under 35 U.S.C. 119 of U.S. Provisional Patent Application No. 61/112,103, filed Nov. 6, 2008, titled "Systems and Methods for Treatment of BPH." These applications are herein incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates to an apparatus and a related method for the minimally invasive treatment of prostate tissue.

BACKGROUND OF THE INVENTION

Several systems and methods have been developed or proposed for the treatment of prostate tissue to alleviate BPH symptoms or to treat prostate tissue. For example, tissue ablation methods have been based on RF ablation, microwave ablation, high intensity focused ultrasound (HIFU), cryoablation, radiation, surgery, and brachytherapy. Surgical methods with and without robotic assistance have been developed for removal of diseased prostate tissue.

The apparatus, techniques and methods disclosed herein are adapted to for the treatment of prostate tissue in general and more particularly are focused on treatment of BPH (benign prostatic hyperplasia) and prostate cancer. BPH is a common problem experienced by men over about 50 years old that relates to urinary tract obstruction. Prostatic hyperplasia or enlargement of the prostate gland leads to compression and obstruction of the urethra which results in symptoms such as the need for frequent urination, a decrease in urinary flow, nocturia and discomfort.

Ablation of prostatic tissue with electromagnetic energy is well known and has the advantage of allowing a less invasive approach. For example, high-frequency current in an electrosurgical ablation or prostatic tissue causes cell disruption and cell death. Tissue resorption by the body's wound healing response then can result in a volumetric reduction of tissue that may be causing urinary tract obstruction. One disadvantage of high-frequency current or laser ablation is potential tissue carbonization that results in an increased inflammatory response and far longer healing time following the ablation.

SUMMARY OF THE INVENTION

A method of extracting tissue from a patient's prostate is provided, comprising, introducing a tissue extraction member into a urethra of the patient, rotating the tissue extraction member within the urethra, injecting condensable vapor from the tissue extraction member, and aspirating prostate tissue into the tissue extraction member.

In some embodiments, the method further comprises injecting high pressure liquid from the tissue extraction member into the urethra. The high pressure liquid can be injected in pulses between 1 pulse/second and 100 pulses/second. In some embodiments, the high pressure liquid is injected radially outward from a longitudinal axis of the tissue extraction member. In other embodiments, the high pressure liquid is injected at an angle of between 10 degrees and 90 degrees from a longitudinal axis of the tissue extraction member.

The method can further comprise expanding an occlusion member within the urethra distal to a tissue extraction member vapor exit port prior to the injecting step. The method can further comprise expanding an occlusion member within the urethra proximal to a tissue extraction member vapor exit port prior to the injecting step.

In some embodiments, the rotating step comprises rotating the tissue extraction member between 5 rpm and 10,000 rpm. The tissue extraction member can be manually rotated, or can be rotated with a powered rotating motor.

In some embodiments, the method further comprises heat sealing tissue margins around extracted tissue in the prostate.

In one embodiment, injecting condensable vapor comprises delivering between 100 W and 1000 W to the prostate. In another embodiment, injecting condensable vapor comprises delivering between 100 cal/gram and 600 cal/gram to the prostate.

In some embodiments of the method, the aspirating step comprises removing between 1 gram and 100 grams of prostate tissue from the prostate.

A prostate therapy system is provided comprising a condensable vapor source, and a tissue extraction member adapted to be inserted into a urethra of an adult male human subject and to rotate within the urethra, the tissue extraction member having a vapor delivery port communicating with the vapor source and adapted to deliver condensable vapor to the prostate lobe and an aspiration port adapted to aspirate prostate tissue proximally into the ablation probe.

The tissue extraction member can further comprise a liquid ejection port communicating with a source of high pressure liquid. In some embodiments, the liquid ejection port and high pressure liquid source are adapted and configured to eject high pressure liquid in pulses between 1 pulse/second and 100 pulses/second. The liquid ejection port is adapted and configured to eject high pressure liquid radially outward from a longitudinal axis of the tissue extraction member. In some embodiments, the liquid ejection port is adapted and configured to eject high pressure liquid at an angle of between 10 degrees and 90 degrees from a longitudinal axis of the tissue extraction member. In one embodiment, the liquid ejection port is concentric with the vapor delivery port.

The prostate therapy system can further comprise a distal occlusion member adapted to occlude the urethra distal to the vapor delivery port, and a proximal occlusion member adapted to occlude the urethra proximal to the vapor delivery port.

In some embodiments, the prostate therapy system further comprises a powered rotating motor configured to rotate the tissue extraction member between 5 rpm and 10,000 rpm.

DETAILED DESCRIPTION OF THE INVENTION

The present invention provides for a vapor energy generation system that can be configured for introduction into a patient's urethra or prostate, or can be configured to access prostatic tissue trans-rectally or endoscopically. The system is configured to deliver a heated vapor, for example water vapor, to tissue as described in the following U.S. patent application Ser. No. 10/681,625, filed Oct. 7, 2003, now U.S. Pat. No. 7,674,259, titled "Medical Instruments and Techniques for Thermally-Mediated Therapies"; Ser. No. 11/158,930, filed Jun. 22, 2005, now U.S. Pat. No. 7,892,229, titled "Medical Instruments and Techniques for Treating Pulmonary Disorders"; Ser. No. 11/244,329, filed Oct. 5, 2005, now U.S. Pat. No. 8,016,823, titled "Medical Instrument and Method of Use"; and Ser. No. 11/329,381, filed Jan. 10, 2006, titled "Medical Instrument and Method of Use".

The generation and delivery of a collapsible, high energy vapor for various therapeutic procedures is further disclosed in systems with "remote" vapor generation systems or sources in Provisional Patent Application Nos. 60/929,632, 61/066,396, 61/068,049, or with vapor generator in a handle or working end, or combination thereof, as described in Provisional Application Nos. 61/068,130, 61/123,384, 61/123,412, 61/126,651, 61/126,612, 61/126,636, 61/126,620.

Figure 1:
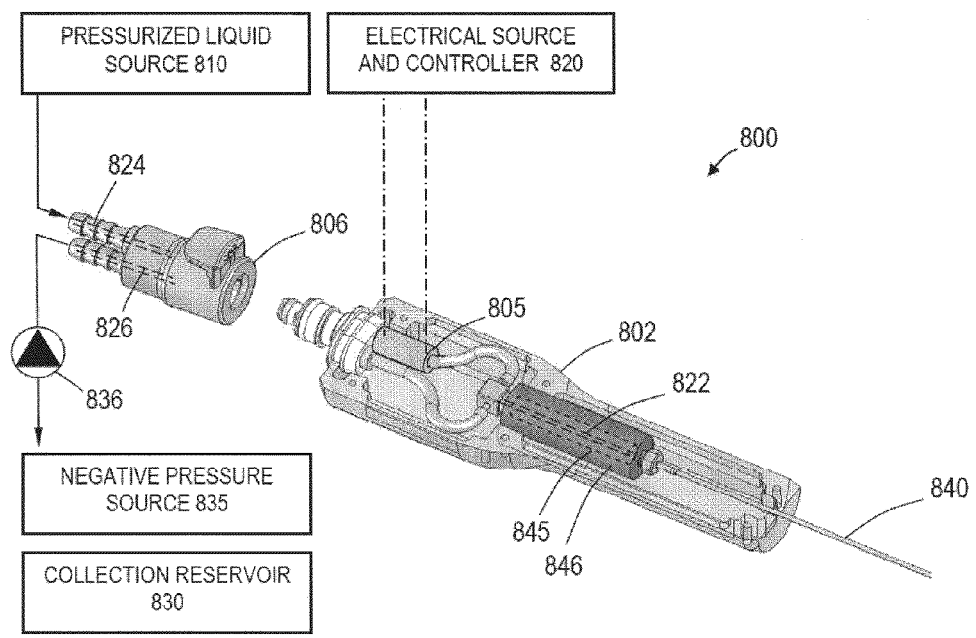
FIG. 1 is a vapor energy delivery system and more particularly a cut-away view of a handle portion of an instrument with an inductive heating assembly for applying vaporization energy to a fluid flow together with a looped flow system for maintaining a circulating flow of high energy vapor which is releasable on demand to flow through an extension member to interact with tissue.

FIG. 1 illustrates a vapor energy generation system 800 having a handle 802 comprising an inductive heating system similar to that described in Provisional Application Nos. 61/123,416, 61/123,417, and 61/126,647. In FIG. 1, the handle 802 is coupled by temperature resistant fitting 806 to a fluid source 810 that delivers liquid at a controlled flow rate and pressure. The liquid flow passes through a vapor generating inductive heater 805 coupled to an electrical source and controller 820. The system and handle is configured for a looped liquid/vapor flow to provide vapor to working end or exit channel 822 to deliver the vapor to a tissue site. The system has inflow channel indicated at 824 and outflow channel at 826 that can communicate with a collection reservoir 830 and/or a negative pressure source 835. A valve 836, for example, operated by a footswitch is provided in outflow channel 826 to re-direct vapor into the exit channel 822 and extension member 840.

A vapor energy generation system 800 as shown in FIG. 1 can be used for any surgical/medical application, with the extension member 840 comprising a needle, an elongate probe or flexible catheter and other similar elongate delivery devices. This system can be used for a catheter for delivering energy for endovascular applications, for treating respiratory tract disorders, for endometrial ablation treatments or for needle ablation treatments. In the embodiment of FIG. 1, an optional secondary heater 845 is shown with a concentric insulator 846. This secondary heater can add further vaporization energy to vapor that starts to flow through exit channel 822. The secondary heater can be an inductive heater or a resistive heater that uses a microporous material to provide a large surface area to apply energy to the vapor to remove any water droplets. This system can provide a vapor that is at least 90% water vapor. The secondary heater is operatively coupled to the electrical source and controller 820 by electrical leads (not shown).

Figure 2:
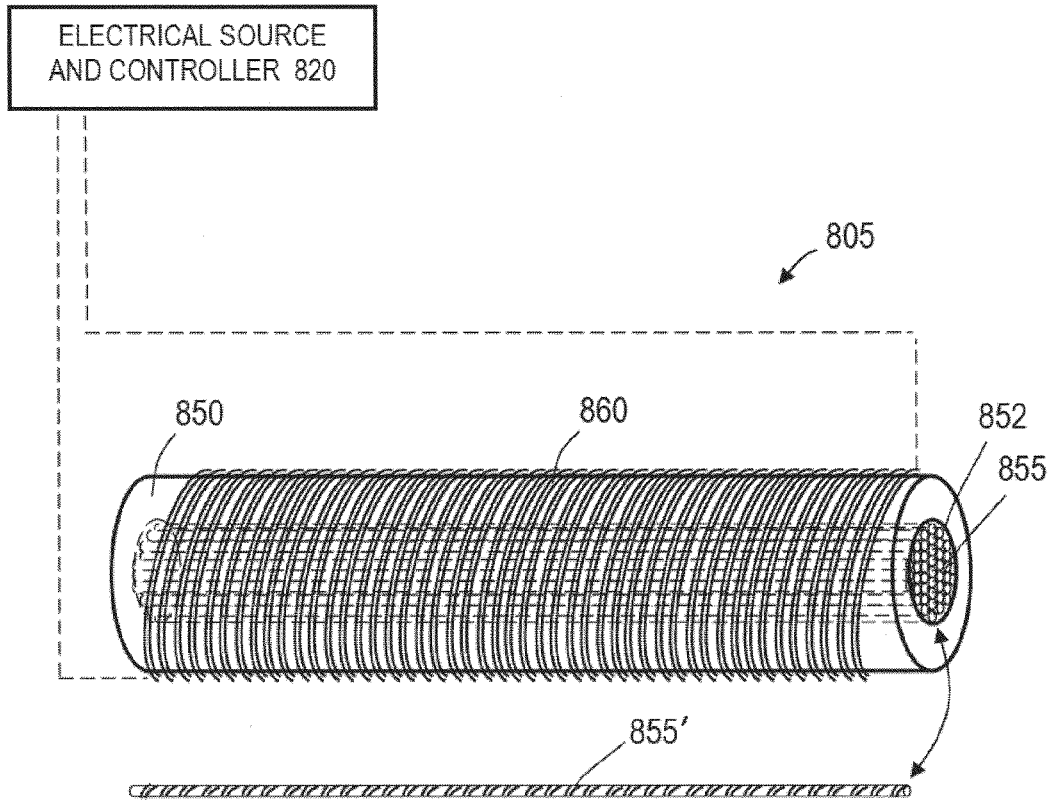
FIG. 2 is a schematic view of the inductive heating assembly of FIG. 1.

FIG. 2 illustrates a vapor generating inductive heater 805 that in one embodiment comprises a ceramic cylinder 850 with a bore 852 therein. The ceramic cylinder 850 can be approximately 1.0" to 1.5" in length and 0.25" in diameter with a 0.10" bore 852, for example. The bore 852 is packed with a plurality of small diameter hypotubes 855 that are magnetic responsive, such as 316 stainless steel, for example. In one embodiment, the hypotubes 855 are 0.016 thin wall tubes. A winding 860 of one to ten layers having an axial length of about 1.0" is provided about the ceramic cylinder 850 for inductive heating of the hypotubes 855 using very high frequency current from an electrical source. In one embodiment the winding 860 can be 26 Ga. Copper wire with a Teflon coating. It has been found that delivering at least 50 W, 100 W, 200 W, 300 W, or 400 W with suitable flow rates of water can produce very high quality vapor, for example 90% vapor and better.

In FIG. 2, it can be seen that an inductively heated hypotube 855' also can be spiral cut to provide flexibility for such an inductive heater to be positioned in a catheter or probe working end. For example, such flexible heatable elements can be carried in the bore of a flexible high temperature resistant polymeric insulative member such to provide a flexible catheter that is configured for endovascular navigation. An insulation layer about an exterior of the inductive heater is not shown. In general, the vapor generating inductive heater 805 can configured to provide a high quality condensable vapor media with precise parameters in terms of vapor quality, exit vapor pressure from a working end, exit vapor temperature, and maintenance of the parameters within a tight range over a treatment interval. All these parameters can be controlled with a high level of precision to achieve controlled dosimetry, whether the particular treatment calls for very low pressures (e.g., 1-5 psi) or very high pressures (200 psi or greater) over a treatment interval, and whether the treatment interval is in the 1-10 second range or 2 to 5 minute range.

Figure 3:
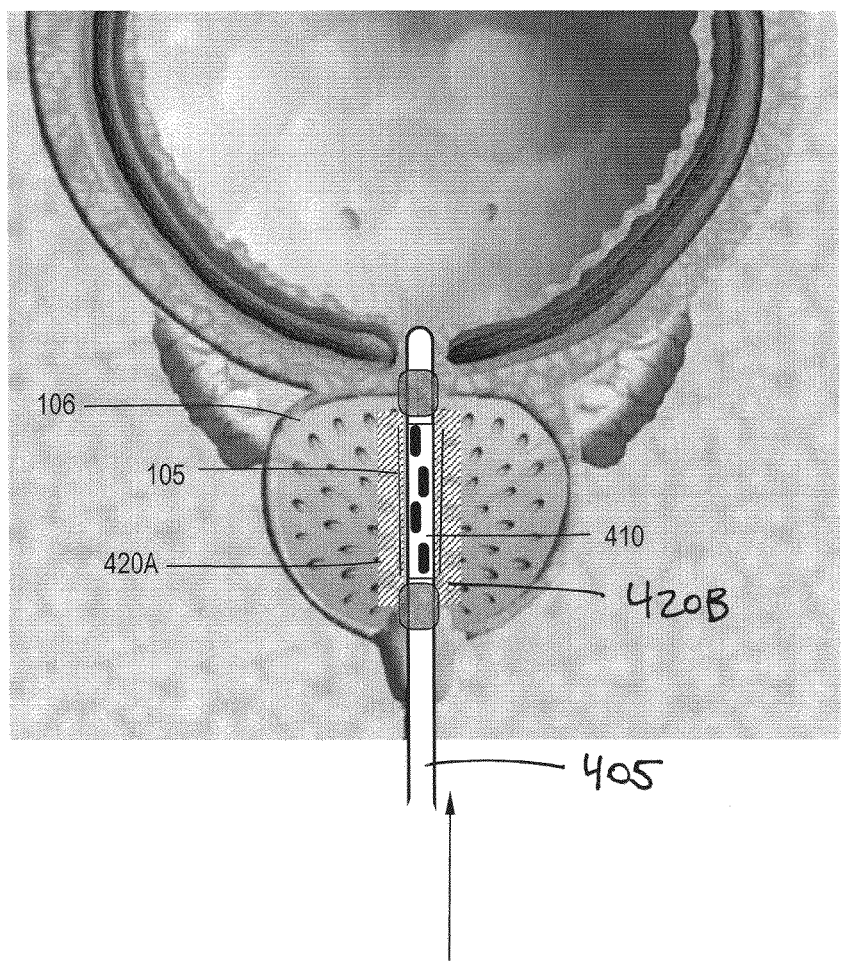
FIG. 3 is a schematic view of a patient prostate and a first step of introducing a tissue extraction member into a patient urethra, showing tissue volumes targeted for extraction.

Now turning to FIG. 3, a sectional schematic view of a patient urethra 105 and prostate 106 is shown with an instrument shaft navigated to a predetermined location in a patient urethra with an imaging system (not shown) to identify anatomical landmarks. An imaging system can be provided in the form of a scope in a channel or a CCD. A system for volumetrically removing prostate tissue is shown with FIG. 3 having an elongate tissue-extraction member 405 with a working end 410 advanced in a transurethral manner into the interior of a patient prostate. The tissue regions indicated at 420A and 420B in the opposing lobes can be targeted for removal. The system also can contemporaneously thermally seal of the margins of the extracted tissue volumes. An irrigation system (not shown) can be provided to supply a fluid to the lumen.

Figure 4:
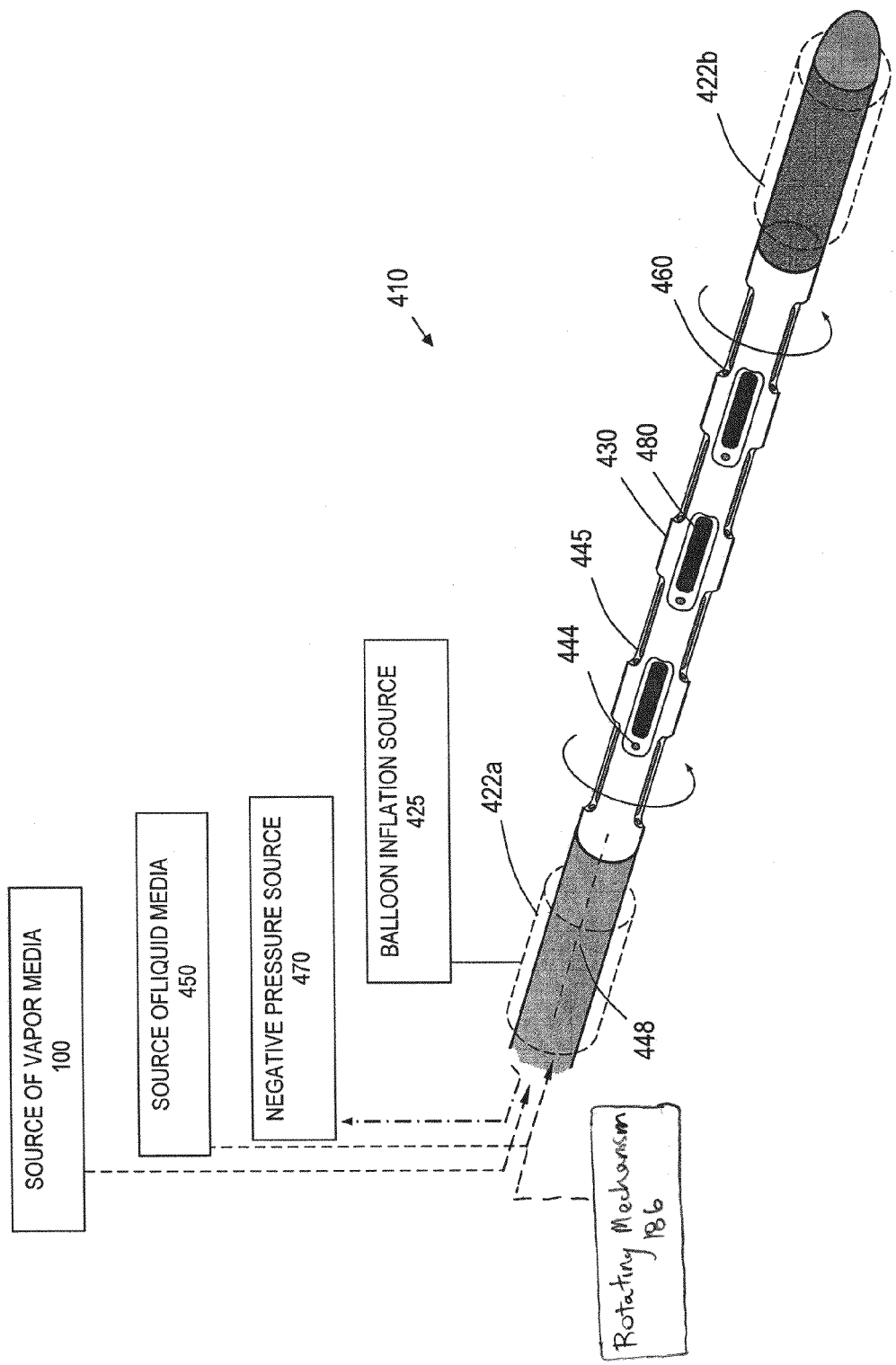
FIG. 4 is a perspective view of an instrument working end.

FIG. 4 illustrates that the tissue extraction member 405 and working end 410 can be a rigid or slightly flexible assembly having a diameter ranging from about 2 mm to 10 mm. The tissue extraction member can include at least one vapor delivery port 444 communicating with a vapor source 100 and can be adapted to deliver condensable vapor to the prostate lobe. The tissue extraction member can also have at least one aspiration port 480 in communication with a negative pressure source 470 and adapted to aspirate prostate tissue proximally into the tissue extraction member. In one embodiment, the tissue extraction member is configured for jetting one of at least one fluid or vapor media from source of liquid media 450, for applying mechanical energy and thermal energy to interfacing tissue for ablation and volumetric removal of urethral tissue and adjacent tissue in a TURP-like procedure.

The working end can carry optional occlusion members 422a and 422b that are expanded by a fluid inflation source 425. The occlusion members can be positioned on the proximal and distal portions of the tissue extracting member. The distal occlusion member 422b is adapted to occlude the urethra distal to the vapor delivery port(s) 444, and the proximal occlusion member 422a is adapted to occlude the urethra proximal to the vapor delivery port(s).

A central portion 430 of the working end is configured to rotate in the body lumen. Rotation of the working end can be manual (e.g., physical rotation of the instrument by the physician) or, alternatively, a rotating mechanism 186 (e.g., a powered rotating motor) can be coupled to the working end 410 to automatically rotate the distal end of the device during ablation and aspiration. The rotating mechanism can be configured to rotate the ablation probe between 5 rpm and 10,000 rpm, for example. Further details of a method of rotating an ablation probe in tissue are described in U.S. patent application Ser. Nos. 12/389,808 and 61/123,416, which are incorporated herein by reference.

Figure 5:
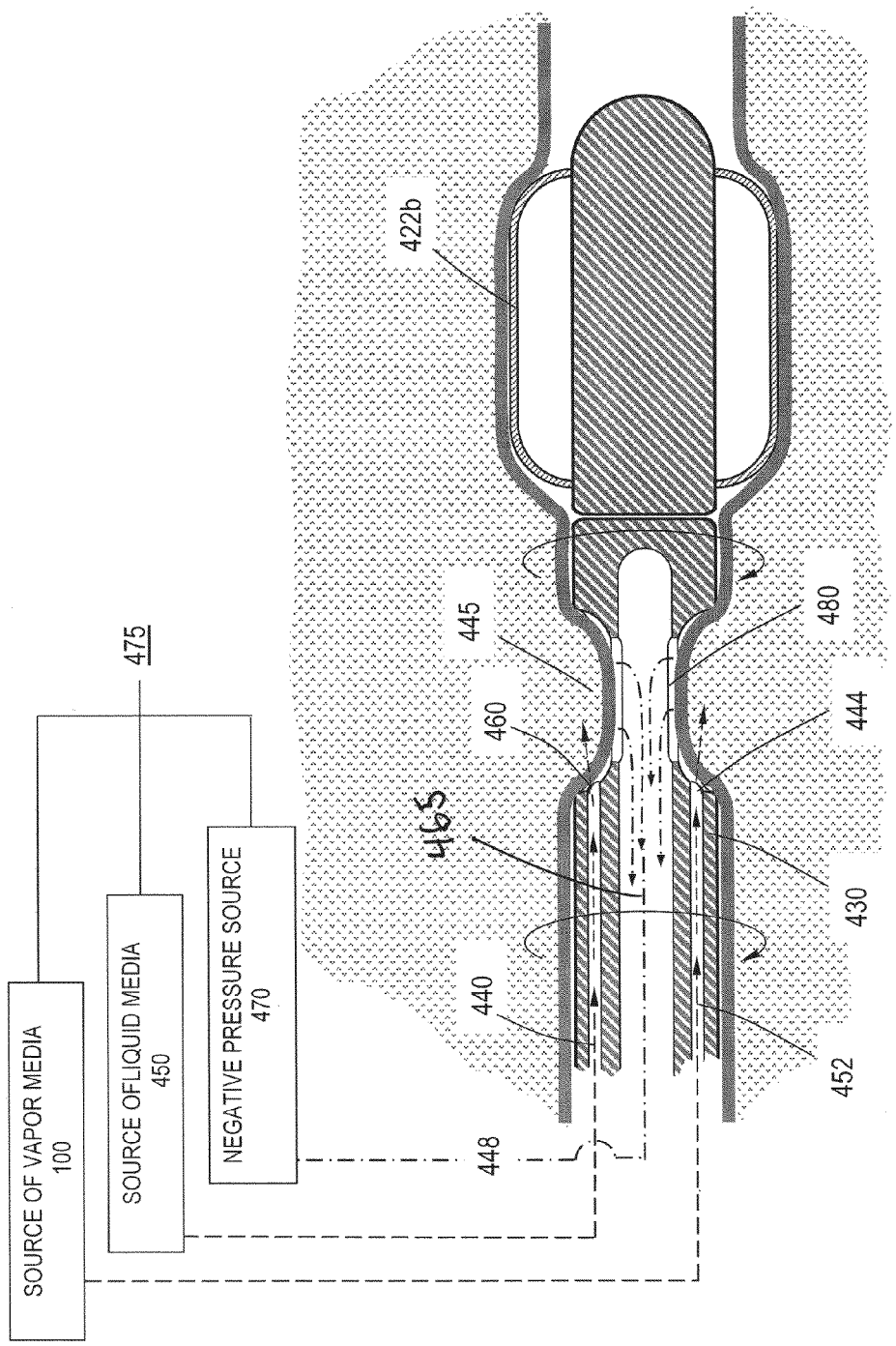
FIG. 5 is a sectional view of the working end of FIG. 4 illustrating schematically how tissue is extracted and sealed.

FIG. 5 shows a sectional view of the instrument working end 410, where it can be seen that a first fluid flow system or condensable vapor source 100 (for example, as shown in FIG. 1) is provided and is fluidly coupled to at least one vapor inflow channel 452 that extends to at least one vapor delivery port 444 in at least one recess 445 in the working end. In this embodiment, the axis of each vapor delivery port can be directed axially relative to the axis 448 of the instrument, or alternatively the axis can be directed radially outwardly from the device axis 448 at an angle of between about 10° to 90° relative to a longitudinal axis 448 of the tissue extraction member.

Still referring to FIG. 5, the instrument working end 410 includes a second fluid flow system comprising a high pressure liquid source 450 that is fluidly coupled to at least one vapor inflow channel 440 that extends to at least one liquid ejection port 460 in at least one recess 445 in the working end. In this embodiment, the axis of each liquid ejection port can be directed substantially axially relative to the axis 448 of the instrument, or alternatively the axis can be directed radially outwardly from the device axis at an angle of between about 10° to 90° relative to a longitudinal axis 448 of the tissue extraction member.

As can be seen in FIG. 5, the instrument working end 410 further includes a tissue extraction channel 465 coupled a negative pressure source 470 for extracting disintegrated tissue, water and condensed vapor media from the treatment site. A computer controller 475 is operatively coupled to the various systems and sources 100, 450 and 470 to allow operation in unison.

Referring to FIG. 5, the instrument working end 410 can actuate the aspiration or negative pressure source 470 and controller 475 to suction tissue into the working end recesses 445 and aspiration port 480, wherein in rotational operation, it can be understood that high pressure ejection of vapor from outlets 444 will cause thermal damage, weakening and denaturation of proteins and tissue constituents. At the same time, the high pressure ejection of liquid media from outlets 460 can disintegrate and disrupt the thermally damaged and weakened tissue to allow its extraction through ports 480. At the same time, the vapor flow and phase change energy release thereof contemporaneously seals or coagulates the tissue margins to prevent bleeding. Following the treatment, the body's wound healing response will heal the urethra as is common in TURP procedures.

It should be appreciated that the working end can have one or more structures for fluid ejection to extract tissue, and can be actuated rotationally and or axially. In one embodiment, the system can be configured to apply energy to tissue about only a selected radial angle of the tissue, for example 5°, 15°, 30°, 45°, 60°, 90° or 180° of the lumen. Similarly, the tissue ablation and extraction can have any axial orientation, for example to ablate and extract linear portions of tissue.

In another method, the working end as in FIGS. 4-5 can be provided without balloons and can be introduced interstitially to extract cores of prostatic tissue.

In another embodiment, a single fluid injection port can be utilized wherein the vapor quality is such that vapor and water droplets in the same flow can apply sufficient mechanical forces to disintegrate and volumetrically remove tissue at the vapor-tissue interface. Thus, in one aspect of the invention, the quality of the vapor, or combination of jetted vapor with jetted water droplets can cut the thermally weakened tissue. In another method, the fluid jet is pulsed at a rate of 1 to 100 pulses/second. In another embodiment, the fluid jetting is pulsed with intermittent pulses of water and vapor at a high repetition rate with the jetted water aliquot capable of disintegrating tissue and the vapor aliquot configured to weaken tissue and thermally seal tissue.

Figure 6:
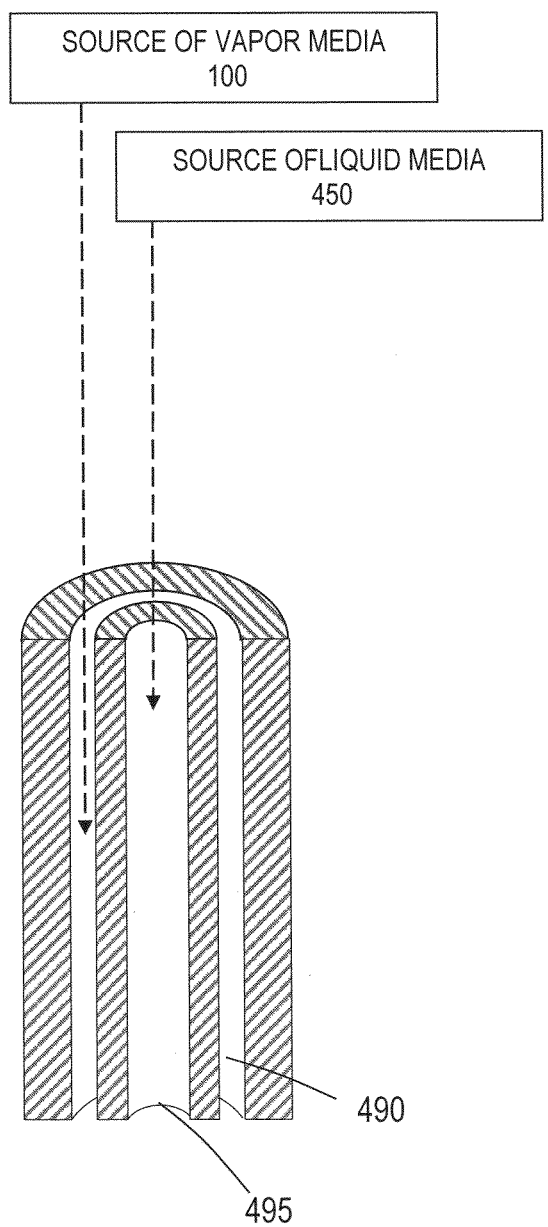
FIG. 6 is a schematic view of another instrument working end.

FIG. 6 illustrates another embodiment of working surface portion wherein a vapor delivery port 490 is concentric around a liquid ejection port 495 for interacting with and ablating tissue. The outlets can be configured is any type of surface structure for ablating tissue such as the recesses of the working end of FIGS. 4 and 5.

In general, a method for treating a prostate disorder comprises volumetrically removing urethra and surrounding prostatic tissue in a method performed with the ejection of jetted liquid and a heated condensable vapor from a device working end together with aspiration of the disintegrated tissue. In one aspect of the invention, the ejection of vapor media applies sufficient thermal energy to substantially modify tissue, wherein the modification consists of at least one of weakening covalent bonds, denaturing proteins and disrupting collagen structures. Further, the ejection of liquid media applies sufficient mechanical energy for tissue removal wherein removal consists of at least one of disintegrating, cutting, excising and ablating tissue. In another aspect of the invention, the ejection of vapor media applies sufficient thermal energy to heat seal or coagulate margins around the extracted tissue. Also, the methods of volumetrically removing tissue can be is performed contemporaneous with imaging, such as ultrasound imaging.

In general, a method for sealing the tissue extracted tissue margins is accomplished with the injecting condensable vapor media from a device working end and aspiration of the disintegrated tissue wherein the energy from the vapor comprises delivering at least 100 W, 250 W, 500 W, and 1000 W to the tissue. In another embodiment, injecting condensable vapor comprises delivering between 100 cal/gram and 600 cal/gram to the prostate.

In general, the method for treating a BPH can volumetrically remove prostatic tissue equaling at least 1 gram, 10 grams, at least 20 grams, at least 30 grams, at least 40 grams, at least 50 grams, and at least 100 grams of tissue.

One embodiment of a method of extracting tissue from a patient's prostate comprises introducing a tissue extraction member into a urethra of the patient, rotating the tissue extraction member within the urethra, injecting condensable vapor from the tissue extraction member, and aspirating prostate tissue into the tissue extraction member. The rotating step can comprise rotating the tissue extraction member between 5 rpm and 10,000 rpm, such as with a powered rotating motor, for example. In another embodiment, the tissue extraction member can be manually rotated.

The method can further comprise injecting high pressure liquid from the tissue extraction member into the urethra. Injection of the high pressure liquid can be injected in pulses between 1 pulse/second and 100 pulses/second. In some embodiments, the high pressure liquid can be injected radially outward from a longitudinal axis of the tissue extraction member. In other embodiments, the high pressure liquid can be injected at an angle between 10 degrees and 90 degrees from a longitudinal axis of the tissue extraction member.

In some embodiments of the method, an occlusion member is expanded within the urethra distal to a tissue extraction member vapor exit port. This step can be performed before injecting condensable vapor from the tissue extraction member, for example. In another embodiment, an occlusion member is expanded within the urethra proximal to a tissue extraction member vapor exit port. This step can be performed before injecting condensable vapor from the tissue extraction member, for example.

In another embodiment, a high speed rotational cutter can be used contemporaneous with a vapor ejection as described above to thermally coagulate the margins about the removed tissue.

A system of the invention comprises an elongated tissue extraction member with a working end configured for removing urethral tissue in a patient prostate, a vapor source in fluid communication with vapor delivery ports in the distal end, a liquid jetting source for ejecting high pressure liquid form the working end and a negative pressure source coupled to a channel in fluid communication with a tissue aspiration port in the working end proximate the vapor delivery ports. The port(s) can be oriented distally relative to an axis of the tissue extraction member, or at an angle relative to an axis of the tissue extraction member, or oriented at a side of tissue extraction member substantially parallel to the axis of the tissue extraction member.

In general, the methods of the invention include delivery of a condensable vapor that undergoes a phase change to provide applied energy of at least 100 cal/gm, 250 cal/gm, 300 cal/gm, 350 cal/gm, 400 cal/gm, 450 cal/gm, and 600 cal/gm of the vapor.

In another aspect of the invention, the treatment with vapor can be accomplished under any suitable type of imaging. In one method, the steps can be viewed by means of ultrasound or x-ray imaging. In one method, the introducer and energy delivery methods of the invention can be imaged by ultrasound utilizing a trans-rectal ultrasound system.

In another aspect of the invention, the system may contemporaneously be used to deliver fluids to targeted locations in the prostate for medical purposes, such as for general or localized drug delivery, chemotherapy, or injections of other agents that may be activated by vapor or heat.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A prostate therapy system comprising:
a condensable vapor source; and
a tissue extraction member adapted to be inserted into a urethra of an adult male human subject and to rotate within the urethra,
the tissue extraction member having a vapor delivery port communicating with the vapor source and adapted to deliver condensable vapor to the prostate lobe, an aspiration port adapted to aspirate prostate tissue proximally into the ablation probe, and a liquid ejection port concentric with the vapor delivery port and communicating with a high pressure liquid source.

2. The system of claim 1 wherein the liquid ejection port and high pressure liquid source are adapted and configured to eject high pressure liquid in pulses between 1 pulse/second and 100 pulses/second.

3. The system of claim 1 wherein the liquid ejection port is adapted and configured to eject high pressure liquid radially outward from a longitudinal axis of the tissue extraction member.

4. The system of claim 1 wherein the liquid ejection port is adapted and configured to eject high pressure liquid at an angle of between 10 degrees and 90 degrees from a longitudinal axis of the tissue extraction member.

5. The system of claim 1 further comprising a distal occlusion member adapted to occlude the urethra distal to the vapor delivery port.

6. The system of claim 1 further comprising a proximal occlusion member adapted to occlude the urethra proximal to the vapor delivery port.

7. The system of claim 1 further comprising a powered rotating motor configured to rotate the tissue extraction member between 5 rpm and 10,000 rpm.

* * * * *